United States Patent [19]

Wilheim

[11] Patent Number: 5,174,164
[45] Date of Patent: Dec. 29, 1992

[54] FLEXIBLE CABLE

[75] Inventor: John J. Wilheim, New Kensington, Pa.

[73] Assignee: Westinghouse Electric Corp., Pittsburgh, Pa.

[21] Appl. No.: 760,629

[22] Filed: Sep. 16, 1991

[51] Int. Cl.⁵ .................... G01D 21/00; G21C 17/017
[52] U.S. Cl. ..................................... 73/866.5; 376/249
[58] Field of Search ........................... 73/866.5, 865.8; 376/249; 254/134.3 FT

[56] References Cited

U.S. PATENT DOCUMENTS

| | | | |
|---|---|---|---|
| 65,715 | 6/1987 | Wright | 254/134.3 FT |
| 938,723 | 11/1909 | Swan | 254/134.3 FT |
| 4,692,957 | 9/1987 | Kovacs | 254/134.3 FT |
| 4,736,978 | 4/1988 | Cielker | 254/134.3 FT |

Primary Examiner—Hezron E. Williams
Assistant Examiner—George Dombroske
Attorney, Agent, or Firm—Walter S. Stevens

[57] ABSTRACT

A flexible cable for carrying an inspection probe along the inside surface of a tube, such as a nuclear steam generator tube, to inspect the tube for anomalies and damage. The cable includes a core member having the inspection probe connected thereto and a plurality of adjacent interconnecting beads surrounding and disposed along the exterior of the core member. Each pair of adjacent beads defines a ball and socket joint for allowing the cable to flex without seizing or doubling-back on itself as the cable is moved in the tube so that the exact location of a tube anomaly can be precisely determined by measuring the length of the cable inserted into the tube.

13 Claims, 7 Drawing Sheets

FLEXIBLE CABLE

This invention generally relates to cables and more particularly relates to a flexible cable for carrying an inspection probe in a tube, such as a nuclear steam generator tube, to inspect the tube for anomalies and damage.

Before discussing the current state of the art, it is instructive first to briefly describe the structure and operation of a typical nuclear steam generator. In this regard, a typical nuclear steam generator generally comprises a shell and a plurality of inverted U-shaped heat transfer tubes disposed in the shell. Radioactive primary fluid (i.e., water), which is heated by a nuclear reactor core, flows through the tubes as nonradioactive secondary fluid (i.e., water) of lower temperature circulates around the tubes. The shell of the steam generator includes a lower plenum portion divided into an inlet plenum chamber and an outlet plenum chamber. A first leg of each inverted U-shaped tube is in fluid communication with the inlet plenum chamber and a second leg of each tube is in fluid communication with the outlet plenum chamber. Also in communication with the inlet plenum chamber is an inlet primary nozzle for delivering the primary fluid into the inlet plenum chamber. Moreover, in fluid communication with the outlet plenum chamber is an outlet primary nozzle for allowing the primary fluid to exit the outlet plenum chamber and thus exit the steam generator.

During operation of the steam generator, the primary fluid, which is heated by the nuclear reactor core, flows from the nuclear reactor core, through the inlet primary nozzle and into the inlet plenum chamber. The primary fluid then flows into the first leg of each tube, out the second leg of each tube and then into the outlet plenum chamber, whereupon it exits the outlet primary nozzle. It should be appreciated that heat is transferred from the primary fluid flowing through the tubes to the secondary fluid circulating around the tubes for generating steam in the interior of the steam generator. The steam is transported to a turbine-generator for producing electricity in a manner well known in the art of steam-powered electricity production. Such a nuclear steam generator is more fully disclosed in U.S. Pat. No. 4,079,701 entitled "Steam Generator Sludge Removal System" issued Mar. 21, 1978 to Robert A. Hickman et al.

Because the primary fluid flowing in the steam generator tubes is radioactive, the steam generator is designed such that the radioactive primary fluid flowing in the tubes does not radioactively contaminate the nonradioactive secondary fluid circulating around the tubes. Therefore, the tubes are designed to be leak-tight so that the radioactive primary fluid remains separated from the nonradioactive secondary fluid to avoid commingling the primary fluid with the secondary fluid.

Occasionally, the steam generator tubes may degrade (i.e., experience tube wall thinning) and develop surface and volume flaws and thus may not remain leaktight. If through-wall cracking occurs due to the flaws or degradation, the radioactive primary fluid may commingle with the nonradioactive secondary fluid. This is undesirable from a safety standpoint. Thus, the steam generator tubes are typically non-destructively examined to determine if any tubes have anomalies that may lead to degradation and to surface and volume flaws. If anomalies are detected, the suspect tube is removed from service such as by plugging the open ends of the degraded tube. On the other hand, the tube, although degraded, may remain in service by sleeving the degraded portion of the tube.

As stated hereinabove, the steam generator tubes are non-destructively inspected to determine if any tubes have anomalies that could lead to surface and volume flaws. The inspection device may be an eddy current or an ultrasonic inspection sensor probe for inspecting the tube. Alternatively, the inspection device may be a combined eddy current and ultrasonic sensor probe. In either case, the eddy current and/or ultrasonic inspection sensor probe is rotatably moved along the inside surface of the tube by a probe carrier to inspect the tube.

However, applicant has observed that the probe carrier can seize (i.e., stick) or buckle such as to double-back (i.e., fold) upon itself in the tube when the probe carrier is subjected to sufficient torsion as it is rotatably moved along the inside surface of the tube. Such a probe carrier will tend to seize or double-back upon itself particularly in the U-bend region of the nuclear steam generator tube. The location of the tube indication is usually determined by measuring the length of probe carrier inserted into the tube. Therefore, if the probe carrier seizes or doubles-back in the tube, the exact location of a tube anomaly or indication sensed by the inspection sensor probe will not be precisely known because the probe carrier will not be completely stretched-out in the tube. It is desirable to know the location of the tube indication in order to later sleeve that region of the tube containing the indication or to obtain a sample of that region of the tube for later metallurgical analysis. Therefore, a problem in the art has been to provide a flexible probe carrier configured to prevent the probe carrier from seizing or doubling-back in the tube, so that the precise location of a tube indication is determinable.

Flexible probe carriers are known. One such probe carrier is disclosed by U.S. Pat. No. 4,901,578 entitled "Probe Carrier Drive Assembly" issued Feb. 20, 1990 to Bernard A. Brill, III and assigned to the Westinghouse Electric Corporation. This patent discloses a probe carrier drive assembly for suitably moving a flexible probe carrier without slip or creep in a tube, the probe carrier having a non-destructive examination device attached thereto. Although this patent discloses a probe carrier that is flexible, this patent does not appear to disclose a flexible cable or a probe carrier configured to prevent the flexible cable or probe carrier from seizing and doubling back in the tube.

An apparatus for conveying a device for inspecting or performing operations on the interior of a tube wall, such as a heat exchanger coil, is disclosed by U.S. Pat. No. 4,050,384 entitled "Tube Inspection And Servicing Apparatus" issued Sep. 27, 1977 to John E. Chapman. This patent discloses a probe lead belonging to the inspection probe and linked to a plurality of traction units spaced along the probe lead. The traction units push the inspection probe through the tube. Although the Chapman patent may disclose a plurality of traction units spaced-along a probe lead, this patent does not appear to disclose a flexible cable or a probe carrier configured to prevent the flexible cable or probe carrier from seizing and doubling-back in the tube.

A flexible probe is disclosed by U.S. Pat. No. 4,413,231 entitled "Eddy Current Inspection Probe For Non-Destructive Inspection Of Tubes With A Probe Body Having An Outer Coiled Spring Sheath And An Inner Plastic Material Sheath" issued Nov. 1, 1983 to Albert Amedro et al. The Amedro et al. patent discloses a flexible probe for nondestructive inspection of long tubes. The measuring head is connected to an electrical connection by means of a body constituted by a sheath that does not deform, according to this patent, either during the introduction of the probe into the tube or during its extraction from the tube. Although the Amedro et al. patent discloses a flexible probe including a body constituted by a sheath, this patent does not appear to disclose a flexible cable or a probe carrier configured to prevent the probe carrier from seizing and doubling-back in the tube.

Thus, although the above recited art may disclose flexible probe carriers movable in a tube, this art does not appear to disclose a flexible cable or probe carrier configured to prevent the flexible cable or probe carrier from seizing and doubling back in the tube.

Therefore, what is needed is a flexible probe carrier or cable configured to prevent the probe carrier or cable from seizing and doubling back in the steam generator tube, so that the precise location of a tube anomaly can be determined by an inspection device connected to the cable or probe carrier.

SUMMARY

Disclosed herein is a flexible cable for rotatably carrying an inspection probe along the inside surface of a tube, such as a nuclear steam generator tube, to inspect the tube for anomalies and damage. The cable includes a central core member having the inspection probe connected thereto and a plurality of adjacent interconnecting hollow beads disposed along and surrounding the exterior of the core member. Any two of the adjacent beads define a ball and socket joint for allowing the cable to flex without seizing or doubling-back on itself as the cable is rotatably moved in the tube, so that the exact location of a tube anomaly can be precisely determined.

More specifically, the cable comprises an elongated flexible core member which has the probe connected thereto. A plurality of adjacent interconnecting tulip-shaped beads are disposed along the core member for providing rigidity and flexibility to the cable. Moreover, each of the beads is made of a low-friction material to prevent its seizing in the tube. Each of the beads has an inner wall defining a bore surrounding the core member. Each of the beads also has a rounded outwardly flared first end portion and a rounded bulbous second end portion, the second end portion defining a generally cup-shaped cavity therein for receiving the first end portion of an adjacent bead. In this regard, the cup-shaped cavity of the second end portion of one bead coacts with the first end portion of an adjacent bead to define a pivotable ball and socket joint. The cavity is in communication with the bore so that the flexible core member extends through the bore and cavity of each bead.

A bearing assembly is interposed between each bead and the core member for allowing transverse rotation of the core member so that the probe, which is attached to the core member, is rotatable. According to the invention, the bearing assembly comprises an annular first ring member, the first ring member having an outer surface connected to the inner wall of the bead and having an inner surface that defines a bore longitudinally through the first ring member, the inner surface having a circumferential groove formed therein. An annular second ring member is disposed in the bore of the first ring member, the second ring member having an outer surface. A plurality of bearings are interposed between the inner surface of the first ring member and the outer surface of the second ring member, each of the bearings being received in the groove of the first ring member. Thus, the second ring member rides on the bearings and is freely rotatable even as the first ring member and the bead connected thereto remain substantially stationary.

An annular flexible retainer is interposed between the second ring member and the core member for retaining the bearings in the groove and for retaining the bearings between the first and second ring members. The retainer has an outer surface connected to the inner surface of the second ring member and an inner surface surrounding the core member. In the preferred embodiment of the invention, the retainer may be a pliable "split" retainer. Such a split retainer defines an open gap through the wall of the retainer, the gap having a predetermined width. The length of the gap extends along the length of the retainer and also extends from the inner surface to the outer surface of the retainer so that the core member may be disposed inside the second ring member by pushing the core member through the gap of the pliable split retainer. The diameter of the second ring member is slightly less than the diameter of the flexible retainer so that the gap of the retainer is substantially reduced as the second ring member compressively snugly surrounds the retainer. Thus, the retainer is captured within the second ring member and the core member is captured inside the retainer. In this manner, the inside surface of the retainer grips or intimately engages the core member so that it is securely connected to the core member by friction.

In the preferred embodiment of the invention, a coaxial electrical conductor wire helically wraps around the length of the core member. The electrical conductor wire, which is wrapped around the core member in a helical fashion, passes through the split or gap in the split retainer and thus passes between the core member and the second ring member. The electrical conductor wire is connected to the inspection probe so that electrical current can be conducted through the electrical conductor wire to the probe to activate the probe and to transmit electrical signals.

A probe pusher is connected to a probe carrier which in turn is connected to the core member for moving the core member and the probe connected thereto along the inside surface of the tube. The probe pusher is also capable of transversely rotating the probe carrier and thus the core member connected thereto. When the core member is rotated by the probe pusher, the electrical conductor wire and the retainer connected thereto also simultaneously rotate to a like extent. As the retainer rotates, the second ring member also rotates because the second ring member is securely connected to the retainer. As the second ring member rotates, it will ride on the bearings that are interposed between the second ring member and the first ring member. However, as the second ring member rides on the bearings, the first ring member, which is connected to the bead, will not substantially rotate. Therefore, each bead will remain substantially stationary because the first ring member, which is connected to the bead, will not substantially rotate. This is so because as the second ring member rides on the bearings, it will slidably rotate within the first ring member. Thus, the core member is capable of transversely rotating while the bead itself remains substantially stationary. In this manner, the flexible cable is configured to prevent the probe carrier from seizing in the tube as the core member is subjected to torsion during its rotation. Moreover, the ball and socket joint configuration of the beads assists in providing a probe carrier that is flexible and also assists in preventing the probe carrier from doubling-back upon itself in the tube as the probe carrier is moved along the inside surface of the tube.

BRIEF DESCRIPTION OF THE DRAWINGS

While the specification concludes with claims particularly pointing out and distinctly claiming the subject matter of the invention, it is believed the invention will be better understood from the following description taken in conjunction with the accompanying drawings, wherein:

DESCRIPTION OF THE PREFERRED EMBODIMENT(S)

Occasionally, nuclear steam generator tubes may develop anomalies or degradation which may lead to surface and volume flaws that could allow the radioactive primary fluid to radioactively contaminate the nonradioactive secondary fluid. Therefore, the steam generator tubes are non-destructively inspected to determine if any tubes have such anomalies that could lead to surface and volume flaws. In this regard, an inspection sensor probe is typically moved along the inside surface of the tube by a flexible probe carrier to inspect the tube. The location of the tube anomaly is determined by measuring the length of probe carrier inserted into the tube. However, the probe carrier can seize (i.e., stick) or double-back (i.e., fold) upon itself in the tube as the probe carrier is rotatably moved in the tube. Consequently, if the probe carrier seizes or doubles-back in the tube, the precise location of a tube anomaly sensed by the inspection probe will not be precisely known because the flexible probe carrier will not be stretched-out in the tube. Therefore, disclosed herein is a flexible cable for carrying an inspection probe in a tube, the cable configured to not seize or double back in the tube so that the precise location of any anomalies or flaws in the tube can be determined.

Before describing the subject matter of the present invention, it is instructive first to generally describe the structure and operation of a typical nuclear steam generator.

Figure 1:
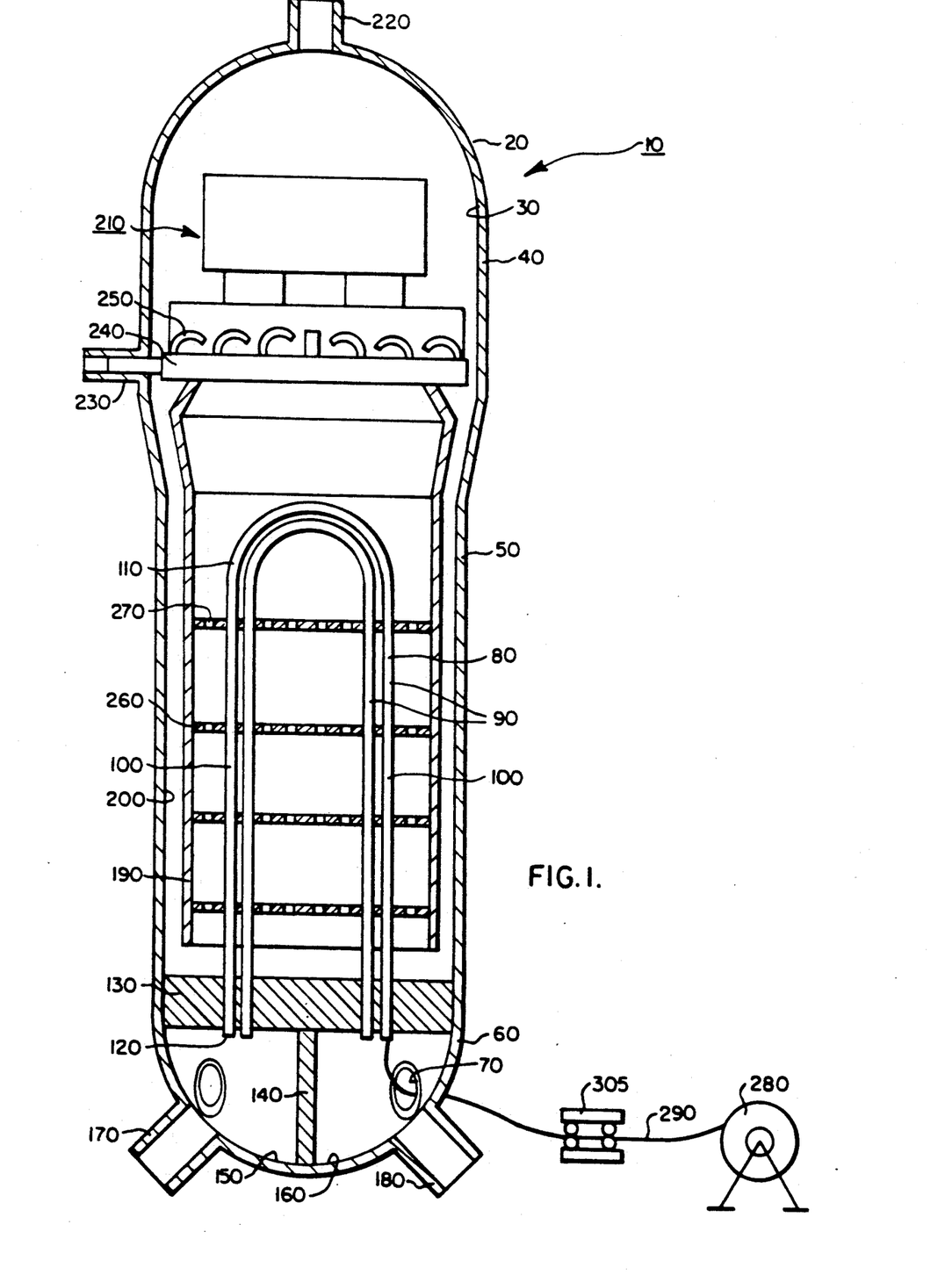
FIG. 1 illustrates a nuclear steam generator, with parts removed for clarity, the steam generator having a plurality of inverted U-shaped heat transfer tubes disposed therein.

Therefore, referring to FIG. 1, there is illustrated a typical nuclear steam generator, generally referred to as 10, for generating steam. Steam generator 10 comprises a vertically-oriented shell 20 defining a cavity 30 therein. Shell 20 has a upper shell portion 40, an intermediate shell portion 50 integrally attached to upper shell portion 40 and a lower shell portion 60 integrally attached to intermediate shell portion 50. Formed through lower shell portion 60 are a plurality of manway openings 70 (only two of which are shown) for providing access to the interior of lower shell portion 60. Of course, manway openings 70 are capable of being sealingly covered by suitable manway covers (not shown) during operation of steam generator 10.

Still referring to FIG. 1, disposed in cavity 30 are a plurality of inverted vertically-oriented U-shaped steam generator tubes 80 for conducting radioactive primary fluid therethrough, the plurality of tubes 80 defining a tube bundle 90. Each U-shaped tube 80, which has an inside surface 95 (e.g., see FIG. 2), has a pair of vertical tube leg portions 100 interconnected by a U-bend tube portion 110 integrally formed therewith. In addition, as shown in FIG. 1, each tube leg portion 100 has an open tube end 120 for passage of the primary fluid therethrough. Disposed in cavity 30 and sealingly attached to lower shell portion 60 is a horizontal tube sheet 130 having a plurality of apertures therethrough for receiving and for vertically supporting each tube end 120, which tube ends 120 are suitably attached to tube sheet 130, such as by welding.

Referring again to FIG. 1, disposed in lower shell portion 60 is a vertical divider plate 140 for dividing lower shell portion 60 into an inlet plenum chamber 150 and an outlet plenum chamber 160. It will be appreciated that manway openings 70 allow access to inlet plenum chamber 150 and outlet plenum chamber 160, so that maintenance can be performed in steam generator 10. Such maintenance may be to inspect certain tubes 80 for anomalies that could eventually lead to through-wall cracks which in turn could allow the radioactive primary fluid to radioactively contaminate the nonradioactive secondary fluid. Integrally attached to lower shell portion 60 is an inlet primary nozzle 170 and an outlet primary nozzle 180 in fluid communication with inlet plenum chamber 150 and with outlet plenum chamber 160, respectively. Moreover, disposed in cavity 30 above tube sheet 130 and interposed between shell 20 and tube bundle 90 is a cylindrical wrapper sheet 190 defining an annular downcomer region 200. Wrapper sheet 190 is open at its bottom end for receipt of secondary feedwater thereinto and partially closed at its top end for passage of a steam-water mixture therefrom. Mounted atop wrapper sheet 190 is a moisture separator assembly, generally referred to as 210, for separating the steam-water mixture into liquid water and relatively dry saturated steam. Moisture separator assembly 210 has holes (not shown) in the bottom portion thereof for receipt of the steam-water mixture rising from the interior of wrapper sheet 190 and holes (not shown) in the top portion thereof for passage of the relatively dry saturated steam flowing upwardly through moisture separator assembly 210. In addition, integrally attached to upper shell portion 40 is a main steam line nozzle 220 for passage of the relatively dry saturated steam therethrough after the dry saturated steam separates from the steam-water mixture and passes upwardly from moisture separator assembly 210.

As shown in FIG. 1, integrally attached to upper shell portion 40 is a feedwater nozzle 230 for passage of nonradioactive feedwater (i.e., secondary fluid) into a feedring 240. After entering feedring 240, the secondary fluid will flow into a plurality of nozzles 250 that are integrally attached to feedring 240 and then flow out nozzles 250 downwardly into downcomer region 200. Disposed inwardly of wrapper sheet 190 are a plurality of horizontal spaced-apart tube support plates 260 (only four of which are shown) having holes 270 therethrough for receiving each tube 80 so that each tube 80 is laterally supported. Each support plate 260 also has a plurality of additional holes for passage of the secondary fluid.

During operation of steam generator 10, the primary fluid, which is heated by a nuclear reactor core (not shown), flows through the inlet primary nozzle 170 and into inlet plenum chamber 150. The primary fluid then travels through the open tube ends 120 that are in fluid communication with inlet plenum chamber 150, through tubes 80, and out the other open tube ends 120 that are in fluid communication with outlet plenum chamber 160. The primary fluid then flows into outlet plenum chamber 160, whereupon the primary fluid exits steam generator 10 through outlet primary nozzle 180. It will be appreciated that as the primary fluid flows through tubes 80, feedwater simultaneously enters steam generator 10 through feedwater nozzle 230, flows through nozzles 250 and then flows downwardly through downcomer region 200 until the feedwater impinges tube sheet 130. The feedwater then turns upwardly to surround tube bundle 90. As the primary fluid flows through tubes 80, it gives up its heat to the secondary feedwater fluid surrounding tube bundle 90. A portion of the secondary feedwater surrounding tube bundle 90 is converted to a steam-water mixture that rises upwardly to moisture separator assembly 210 which separates the steam-water mixture into liquid water and relatively dry saturated steam. The liquid water returns downwardly to tube bundle 90 as the dry saturated steam continues upwardly to exit steam generator 10 through main steam line nozzle 220. The steam then travels to a turbine-generator (not shown) for producing electricity in a manner well known in the art of steam-powered electricity production. Such a steam generator is disclosed in U.S. Pat. No. 4,079,701 entitled "Steam Generator Sludge Removal System" issued Mar. 21, 1978 to Robert A. Hickman et al., the disclosure of which is hereby incorporated by reference.

As stated hereinabove, some of the tubes 80 may develop anomalies that could lead to surface and volume flaws. Consequently, tubes 80 are non-destructively examined or inspected to determine if any such tubes 80 have anomalies that could lead to surface and volume flaws.

Therefore, as shown in FIG. 1, a take-up reel 280 is provided, around which take-up reel 280 is wound a flexible probe carrier 290 having an inspection probe assembly 300 (see FIG. 2) connected thereto for inspecting a preselected tube 80 for anomalies. Inspection probe assembly 300 may be an eddy current inspection probe assembly capable of suitably detecting and measuring indications (i.e., anomalies) in tube 80 by generating electromagnetic eddy currents in tube 80. Alternatively, inspection probe assembly 300 may be an ultrasound testing device selected from those readily available in the art for suitably transmitting sound waves through tube 80 in a manner such that any anomalies in tube 80 are detected. As shown in FIG. 1, probe carrier 290 is capable of being engaged by a probe pusher 305 for inserting or pushing inspection probe 300 through manway 70 and through open tube end 120 and for rotatably moving (e.g., pushing) inspection probe 300 along inside surface 95 of tube 80 so that the precise locations of any tube anomalies are detected.

Figure 2:
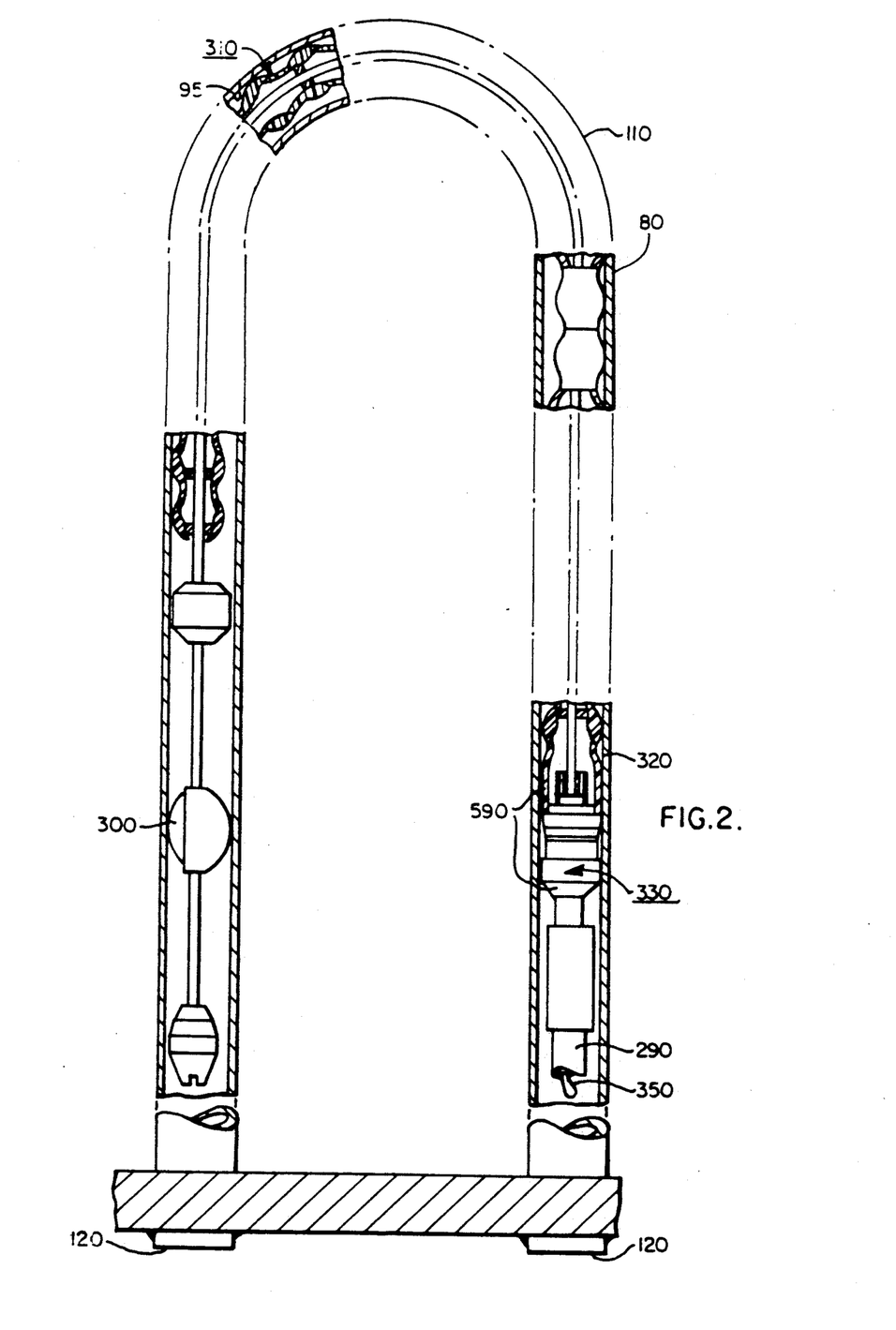
FIG. 2 is a view in partial vertical section of a flexible cable disposed in one of the tubes.
Figure 3:
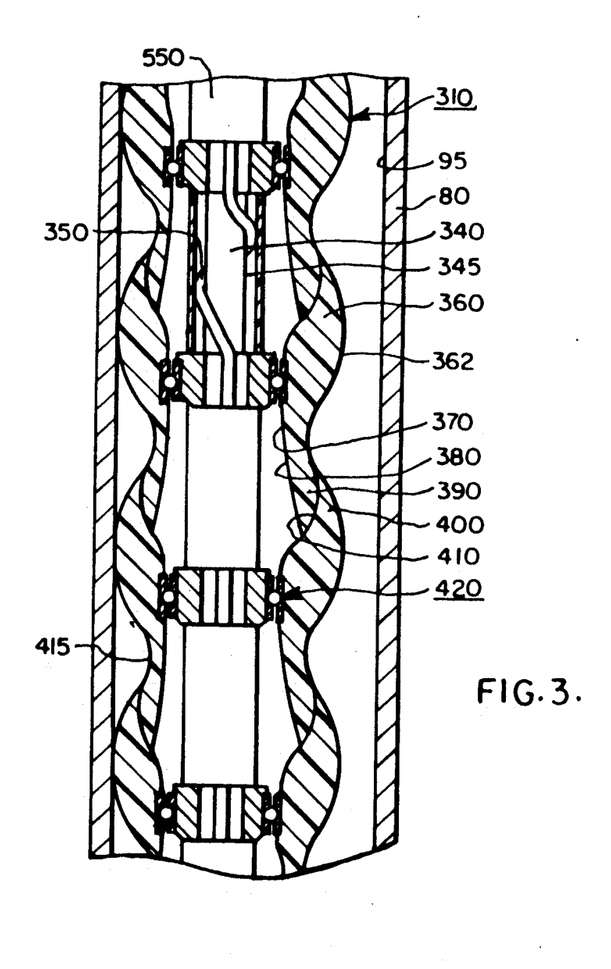
FIG. 3 is a fragmentation view in partial vertical section of the cable disposed in the tube, the cable comprising a plurality of interconnecting beads.
Figure 4:
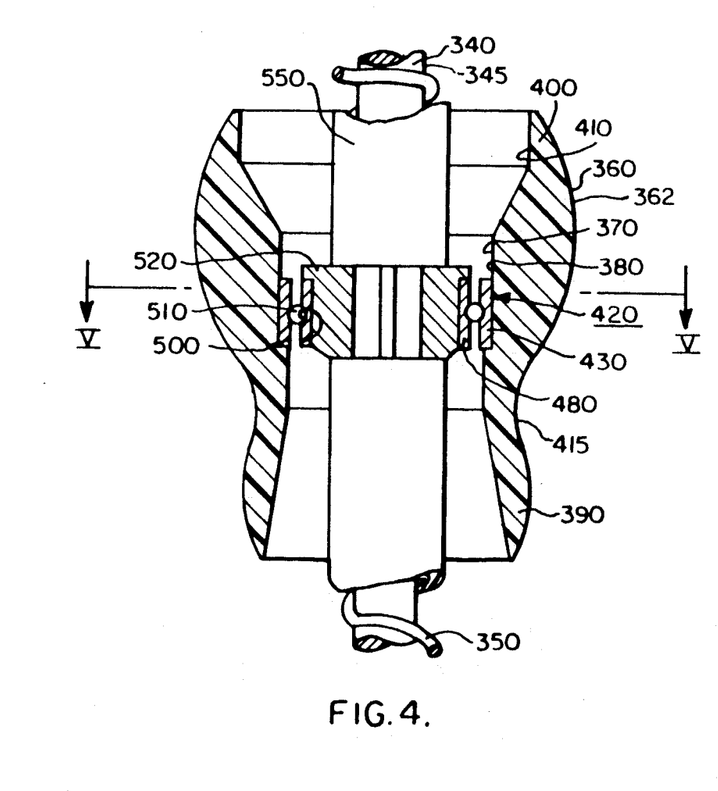
FIG. 4 is a view in partial vertical section of one of the beads.

Referring now to FIGS. 2 and 3, there is shown a flexible cable generally referred to as 310 for rotatably carrying eddy current inspection probe 300, which is connected thereto, along inside surface 95 of tube 80 to inspect tube 80. As described in more detail hereinbelow, cable 310 may have a proximal end portion 320 capable of being connected to an eddy current reference probe assembly, generally referred to as 330, which in turn is connected to probe carrier 290. In the preferred embodiment, inspection probe assembly 300 and reference probe assembly 330 are eddy current probes capable of generating electromagnetic eddy currents in those portions of tube 80 respectively adjacent thereto. It will be understood that, alternatively, inspection probe assembly 300 and reference probe assembly 330 may be ultrasonic testing devices selected from those readily available in the art for sonically inspecting tube 80.

Still referring to FIGS. 2 and 3, cable 310 comprises an elongated generally cylindrical flexible core member 340 having an exterior surface 345 and having inspection probe assembly 300 connected to a distal end portion thereof and also having reference probe assembly 330 connected to the proximal end portion 320 thereof. Thus, cable 310 supports thereon inspection probe assembly 300 and reference probe assembly 330. As used herein, the words "distal end portion" is defined to mean that end portion of cable 310 that is further away from the tube end 120 through which cable 310 is inserted and the words "proximal end portion" is defined to mean that end portion of cable 310 that is nearest to the tube end 120 through which cable 310 is inserted. In the preferred embodiment of the invention, core member 340 may be helically wound layered steel for providing resistance to shear stress as well as for providing durability and flexibility to core member 340. For these purposes, core member 340 preferably may be layered carbon steel or stainless steel. Core member 340 has one or more elongated electrical conductors 350 helically wound therearound and extending along the length thereof, electrical conductors 350 being connected to inspection probe assembly 300 and to reference probe assembly 330 for conducting electrical current to probe assemblies 300 and 330. In the preferred embodiment of the invention, the electrical current flowing to inspection probe assembly 300 and reference probe assembly 330 causes electromagnetic waves to emanate therefrom so that electromagnetic eddy currents are generated in tube 80 for detecting anomalies in tube 80.

Referring again to FIGS. 2 and 3, disposed along and surrounding the exterior of core member 340 are a plurality of adjacent interfacing and interconnecting hollow beads 360 for simultaneously providing rigidity and flexibility to cable 310. Of course, each bead 360 is of a maximum diameter smaller than the inside diameter of tube 80 and may be a material, such as plastic, having a low coefficient of friction for allowing each bead 360 to slide or glide with minimal friction along inside surface 95 of tube 80, so that cable 310 will not seize in tube 80. For this purpose, each bead 360 may be "DELRIN" polyethylene plastic or the like. Each of the beads 360 defines a tulip-shaped shell 362 having an inner wall 370 defining a longitudinal bore 380 therethrough surrounding core member 340. For purposes described more fully hereinbelow, each bead 360 also has a generally rounded outwardly flared first end portion 390. Moreover, each bead 360 has a generally rounded bulbous second end portion 400 defining a generally cup-shaped cavity 410 therein in communication with bore 380. Cavity 410 pivotably receives first end portion 390 belonging to an adjacent bead 360. Intermediate the first end portion 390 and the second end portion 400 is a concave intermediate portion 415 integrally formed with first end portion 390 and second end portion 400 for reasons provided hereinbelow. Therefore, it will be understood that in the preferred embodiment, shell 362 defined by each bead 360 is generally tulip-shaped in transverse cross section. Viewed another way, each cavity 410 together with each first end portion 390 that is received in cavity 410 coact to provide a ball and socket joint pivotally interconnecting each bead 360 with its associated adjacent bead. In this manner, all beads 360 are pivotally interconnected for providing flexibility to cable 310, as described in more detail hereinbelow.

Figure 5:
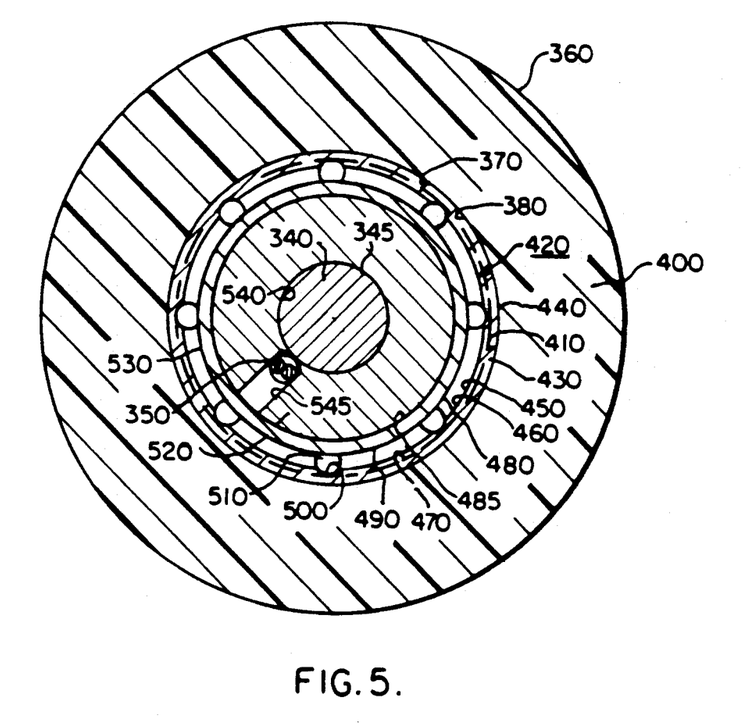
FIG. 5 is a view in horizontal section of one of the beads taken along section line V—V of FIG. 4.
Figure 5A:
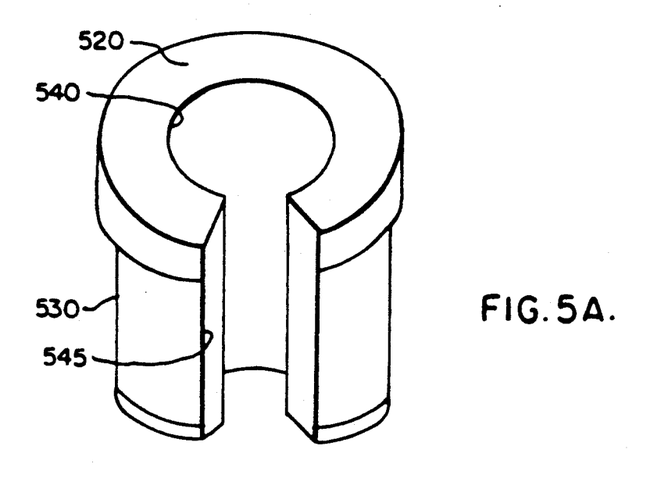
FIG. 5A is an orthogonal view of a retainer member capable of being disposed in each of the beads.

As best seen in FIGS. 3, 4, 5 and 5A, cable 310 further comprises a bearing assembly, generally referred to as 420, which is interposed between each bead 360 and core member 340 for allowing transverse rotation of core member 340 about its longitudinal axis. Thus, it will be appreciated that inspection probe assembly 300 and reference probe assembly 330, which are connected to core member 340, are freely transversely (i.e., radially) rotatable in tube 80. It is important that cable 310 include bearing assembly 420. This is important because inspection probe assembly 300 and reference probe assembly 330 must be transversely rotatable so that tube 80 can be radially inspected as it is simultaneously longitudinally inspected for anomalies. Each bearing assembly 420 includes an annular outer race or first ring member 430 disposed in bore 380 of bead 360, first ring member 430 having an outer surface 440 affixed or connected to inner wall 370 of bore 380. First ring member 430 may be affixed or connected to inner wall 370 by any suitable means, such as by a press fit. First ring member 430 also has an inner surface 450 defining a longitudinal bore 460 through first ring member 430. In the preferred embodiment, inner surface 450 has a groove 470 therein, as shown (exaggerated for clarity) by the phantom dotted circular line in FIG. 5, for reasons described presently. In the preferred embodiment, groove 470 extends around inner surface 450. Alternatively, inner surface 450 may have a plurality of aligned circumferentially spaced-apart hemispherical recesses 500 formed therein, as shown in FIG. 5, for reasons described presently. Each bearing assembly 420 also includes an annular inner race or second ring member 480 defining an inner surface 485, second ring member 480 being disposed in bore 460 of first ring member 430. Second ring member 480 has an outer surface 490 which is smooth. A plurality of generally spherical bearings 510 are interposed between first ring member 430 and second ring member 480. Each bearing 510 is sized to be matingly rotatably received in groove 470. Alternatively, each bearing 510 may be sized to be matingly rotatably received in its associated recess 500. It will be understood that this structure allows second ring member 480 to freely rotate within first ring member 430 for reasons provided hereinbelow. As best seen in FIGS. 5 and 5A, bearing assembly 420 also includes an annular retainer member 520 interposed between second ring member 480 and core member 340 for retaining bearings 510 between first ring member 430 and second ring member 480. Retainer 520 has an outer surface 530 affixed or connected to inner surface 485 of second ring member 480 and also an inner surface 540 surrounding and engaging exterior surface 345 of core member 340. In the preferred embodiment of the invention, retainer 520 may be a pliable "split" retainer. Such a pliable split retainer 520 defines an open gap 545 therethrough of predetermined width along its length and transversely extending from inner surface 540 to outer surface 530 so that core member 340 may be disposed inside second ring member 480 by pushing core member 340 through gap 545. Open gap 545 also provides a passageway sized for passage of electrical conductors 350 within gap 545. Hence, as core member 340 rotates, retainer 520 also rotates because retainer 520 grippingly engages core member 340. Moreover, as retainer 520 rotates, second ring member 480 also rotates because second ring member 480 is connected to retainer 520. In this manner, core member 340, retainer 520 and second ring member 480, which second ring member 480 rides on bearings 510, are freely transversely rotatable within first ring member 430 so that core member 340 and the probes 300/330 connected thereto are transversely rotatable.

Still referring to FIGS. 3, 4, 5 and 5A, cable 310 may further comprise a generally cylindrical flexible sheath 550 surrounding core member 340 and interposed between adjacent retainers 520 for protecting core member 340 from damage, as well as for protecting the electrical conductor 350 helically extending around core member 340. Also, each sheath 550 is interposed between adjacent retainers 520 for fixing the location of each retainer axially on core member 340. Sheath 550 may be a flexible material, such as plastic, for allowing cable 310 to be flexible. For this purpose, sheath 550 may be "DELRIN" polyethylene or plastic, or the like.

Figures 6, 7:
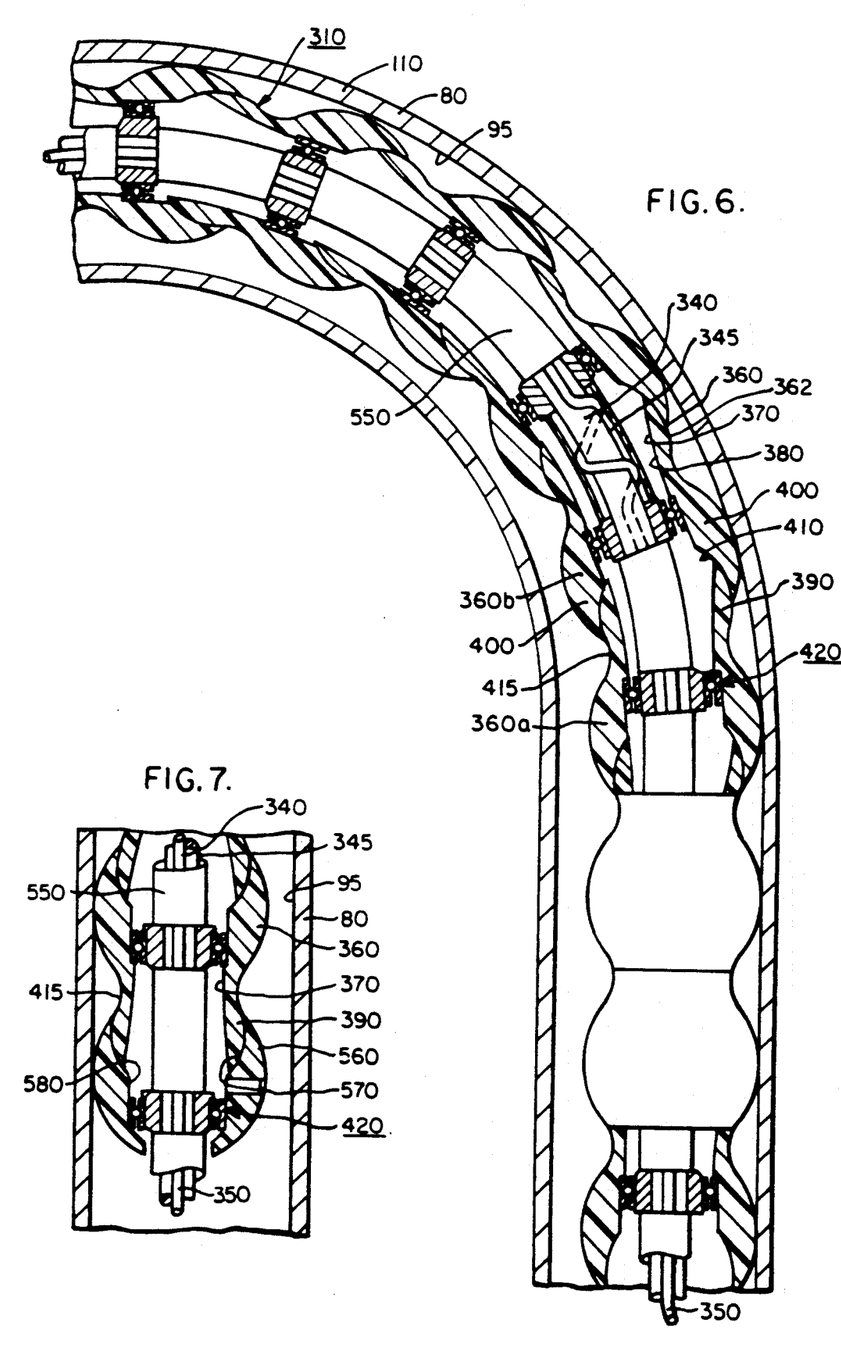
FIG. 6 is a view in partial vertical section of the cable in a flexed condition inside the U-bend portion of the tube.
FIG. 7 is a fragmentary view in partial vertical section of the distal end portion of the cable.

Referring now to FIG. 6, a portion of flexible cable 310 is there shown disposed in the U-bend region 110 of tube 80. As seen in FIG. 6, the ball and socket configuration of any two adjacent beads 360 belonging to cable 310 allows cable 310 to flex in order to follow the contour of U-bend region 110, as cable 310 moves along inside surface 95 of U-bend region 110, in such a manner that cable 310 does not double-back (i.e., fold) within tube 80. This is so because first end portion 390 of bead 360a will engage cavity 410 of its associated adjacent bead 360b only to the extent where second end portion 400 of bead 360b engages intermediate portion 415 of bead 360a, as illustrated in FIG. 6. When second end portion 400 of bead 360a engages intermediate portion 415 of bead 360a the pivoting action of the bead 360b will cease because the sloping sides of concave intermediate portion 415 will obstruct the further movement of second end portion 400 and thus will prevent bead 360b from pivoting further. Therefore, limiting the pivoting action of each bead 360 will prevent cable 310, which comprises the plurality of beads 360, from substantially folding or doubling-back upon itself in tube 80 and also will provide cable 310 with a predetermined amount of rigidity. Preventing cable 310 from folding or doubling-back upon itself in tube 80 assists in precisely detecting the axial location of any tube indications or anomalies present in tube 80, as described more fully hereinbelow.

Figure 8:
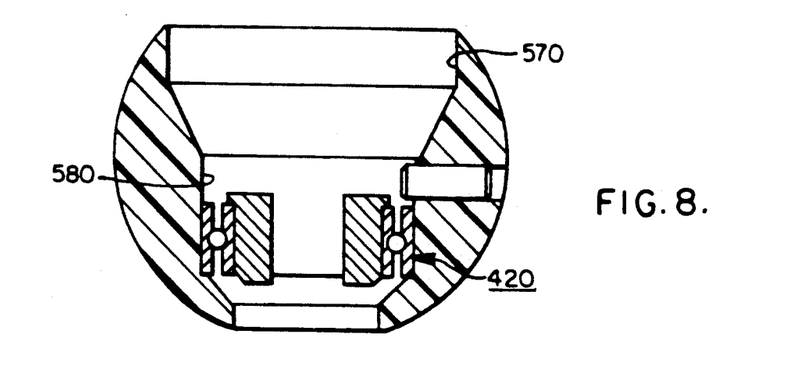
FIG. 8 is a view in vertical section of a distal end bead belonging to the distal end portion of the cable.

Turning now to FIGS. 7 and 8, cable 310 may further comprise a distal end bead 560 connected thereto for allowing cable 310 to be easily insertable into open tube end 120 without snagging on open tube end 120. In this regard, distal end bead 560 is generally spherically-shaped and has an open cavity 570 sized for pivotally receiving therein first end portion 390 of its associated adjacent bead 360. Distal end bead 560 also has a bore 580 therethrough in communication with open cavity 570. Extending through cavity 570 and bore 580 is core member 340. Moreover, disposed in bore 580 and surrounding core member 340 is bearing assembly 420. It will be appreciated that the generally spherical shape of distal end portion 560 allows distal end portion 560 and the remainder of cable 310 connected thereto to be easily slidably inserted into open tube end 120 without snagging on open tube end 120.

Figure 9:
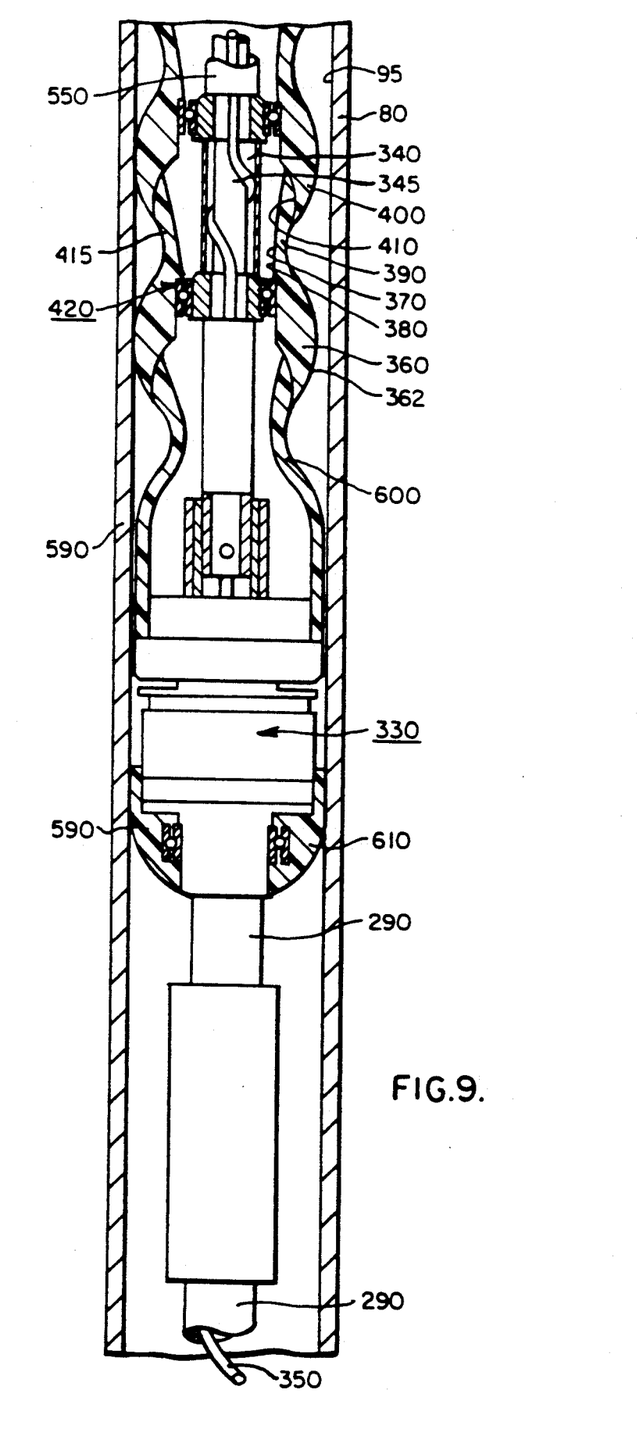
FIG. 9 shows in vertical section the proximal end portion of the cable.
Figure 10:
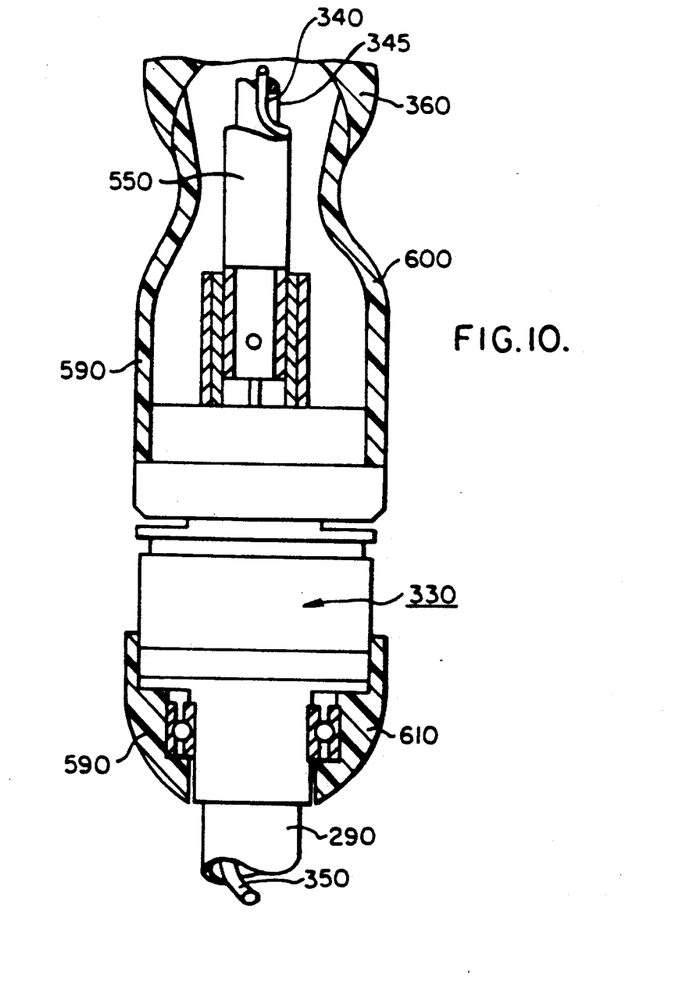
FIG. 10 is a view in vertical section of a proximal end bead assembly belonging to the proximal end portion of the cable.

Referring to FIGS. 9 and 10, cable 310 may include a proximal end bead assembly 590 connected to proximal end portion 320 for pivotably attaching cable 310 to reference probe assembly 330. Proximal end bead assembly 590 may include a tulip-shaped bead 600 pivotally interconnecting an adjacent bead 360 with reference probe assembly 330. It will be appreciated that this structure, which interconnects cable 310 with reference probe assembly 330, defines a pivotable joint between cable 310 and reference probe assembly 330. This pivotable joint maintains the proximal end portion 320 of cable 310 in a flexible condition as cable 310 is moved along inside surface 95 by probe pusher 305.

By way of example only and not by way of limitation, nuclear steam generator tube 80 may be "INCONEL 600" for resisting corrosion and may have an outside diameter of approximately 0.875 inches and a wall thickness of approximately 0.050 inches. Rounded second end portion 400 of each bead 360 may have a maximum outside diameter of approximately 0.674 inches so that each bead is insertable within tube 80. The rounded portion of second end portion 400 may have a radius of curvature of approximately 0.250 inches. Cavity 410, which is formed in second end portion 400, may have a maximum diameter of approximately 0.505 inches for matingly pivotally receiving first end portion 390 of an adjacent bead 360. Concave intermediate portion 415, which integrally connects first end portion 390 and second end portion 400, may have a radius of curvature of approximately 0.150 inches. Each bore 380, which extends through each bead 360, may have a diameter of roughly 0.382 inches. First ring member 430, which is affixed in bore 380, may have an outside diameter of approximately 0.375 inches and an inside diameter of approximately 0.330 inches and may be approximately 0.125 inches wide in transverse cross section. Second ring member 480, which is disposed inside first ring member 430, may have an outside diameter of roughly 0.295 inches and an inside diameter of approximately 0.250 inches. Spherical bearing 510, which is interposed between first ring member 430 and second ring member 480 in the configuration disclosed hereinabove, may have a diameter of roughly 0.065 inches. Retainer 520, which is disposed within second ring member 480, may have an outside diameter of approximately 0.254 inches and an inside diameter of approximately 0.126 inches for surrounding core member 340. Core member 340, which is disposed within retainer 520, may have an outside diameter of approximately 0.128 inches. Each sheath 550, which is interposed between adjacent retainers 520 and which surrounds core member 340, may have an outside diameter of approximately 0.260 inches and an inside diameter of approximately 0.250 inches. Of course, electrical conductors 350 may be copper wire conductors for conducting electrical current to probes 300 and 330 and are sized to pass through gap 545.

OPERATION

First, steam generator 10 is taken out of service and drained of primary and secondary fluids in a manner well known in the art. Next, the manway covers (not shown) that cover manway openings 70 are removed. Probe pusher 305, which is caused to engage probe carrier 290, is operated to unwind probe carrier 290 from take-up reel 280. As probe carrier 290 is unwound from take-up reel 280, the distal end portion of probe carrier 290 (and cable 310 which is connected thereto) is inserted into open tube end 120. Probe pusher 305 is then suitably operated such that inspection probe assembly 300 and reference probe assembly 330 rotatably move along inside surface 95 of tube 80 for detecting anomalies in tube 80.

As disclosed hereinabove, core member 340 is rotated by probe carrier 290 to rotate inspection probe assembly 300 and reference probe assembly 330. As, core member 340 rotates, retainer 520 will rotate to a like extent. As retainer 520 rotates, second ring member 480 will rotate and ride on bearings 510 which are interposed between second ring member 480 and first ring member 430. It will be appreciated that as second ring member 480 rotates, first ring member 430 will necessarily remain stationary because bearings 510 slidably separates first ring member 430 from second ring member 480. In this manner, core member 340 rotates without necessarily rotating shell 362 defined by bead 360. This is important because allowing core member 340 to rotate without rotating shell 362 assists in preventing seizing and knotting of cable 360 in tube 80.

Cable 310 will tend to undulate or flex, particularly in the U-bend region 110 of tube 80, as probe pusher 305 pushes cable 310 along the inside surface 95 of tube 80. If beads 360 were not present (i.e, only core member 340 present), then there will be an increased likelihood that torsion will cause core member 340 to knot and double-back upon itself and then seize in tube 80 as it is being rotatably pushed by probe pusher 305. However, as will be disclosed presently, the presence of beads 360 prevents core member 340 from doubling-back upon itself and seizing in tube 80 in order that the precise location of a tube indication can be determined. In this regard, as first end portion 390 of bead 360a slidably pivotally engages cavity 410 of an associated adjacent bead 360b when cable 310 is flexed, bead 360a will pivot in cavity 410 (see FIG. 6). The pivoting action of bead 360a will continue until the leading edge of second end portion 400 of bead 360b engages concave intermediate portion 415 of bead 360a. Moreover, beads 360a and 360b are sized such that as bead 360a pivots to this maximum extent, first end portion 390 of bead 360a will not clear or leave cavity 410 of bead 360b, as shown in FIG. 6. That is, the pivot angle of bead 360a is limited by the amount of concavity of intermediate portion 415 as second end portion 400 engages concave intermediate portion 415. Thus, when cable 310 is used for its intended purposes, cable 310 will not double-back or seize in tube 80 because the angle through which cable 310 will bend is restricted or limited by the concavity of intermediate portion 415. However, it should be understood that complete rigidity of cable 310 is undesirable because cable 310 must be capable of bending for navigating U-bend region 110 of tube 80. On the other hand, complete flexibility of cable 360 is also undesirable because cable 310 must be capable of not doubling-back on itself or seizing. Thus, cable 310 is both sufficiently rigid as well as sufficiently flexible for suitably moving in tube 80.

After tube 80 has been inspected, the tube inspection device is removed from steam generator 10 in substantially the reverse order of its installation into steam generator 10. Tubes 80 that have indications are then either sleeved in the region of the indication or plugged. After the appropriate steam generator tubes 80 have been sleeved or plugged, the manway covers are replaced over manway openings 70 and steam generator 10 is returned to service.

Although the invention is fully illustrated and described herein, it is not intended that the invention as illustrated and described be limited to the details shown, because various modifications may be obtained with respect to the invention without departing from the spirit of the invention or the scope of equivalents thereof. For example, core member 340 need not be layered steel; rather, core member 340 may be any suitable material resistant to sheer stress while remaining flexible. Moreover, the transverse cross section of each bead 360 need not be as shown in the several figures; rather, the transverse cross section of each bead 360 may be any suitable cross section for limiting the pivoting action of beads 360 while maintaining cable 360 in a flexible condition.

Moreover, although the invention was conceived during an investigation directed towards flexible cables for carrying inspection devices in nuclear steam generator tubes, it will be appreciated that the invention may have other uses, such as flexible cables for any purpose where the use of a flexible cable is appropriate.

Therefore, what is provided is a flexible cable suitable for use in a tube, the flexible cable configured to prevent the cable from seizing or doubling back in the tube.

What is claimed is:

1. A flexible cable, comprising:
   (a) an elongated flexible core member;
   (b) a plurality of adjacent interconnecting beads disposed along said core member, each of said beads having an inner wall defining a bore therethrough surrounding said core member; and
   (c) a plurality of bearing assemblies each interposed between each of said beads and said core member.

2. The flexible cable of claim 1,
   (a) wherein each of said beads has a flared first end portion; and
   (b) wherein each of said beads has a second end portion defining a cavity therein in communication with the bore for matingly receiving the flared first end portion of an adjacent bead.

3. The cable of claim 2, wherein each of said bearing assemblies comprises:
   (a) an annular first ring member connected to the inner wall of said bead;
   (b) an annular second ring member disposed within said first ring member;
   (c) an annular retainer disposed within said second ring member and surrounding said core member, said retainer slidably rotatably connected to said second ring member; and
   (d) a bearing interposed between said first ring member and said second ring member.

4. A flexible cable for carrying an inspection probe, comprising:
   (a) an elongated flexible core member having the probe connected thereto for supporting the probe;
   (b) a plurality of adjacent interconnecting beads disposed along said core member for providing rigidity and flexibility to said cable, each of said beads having an inner wall defining a bore therethrough surrounding said core member; and
   (c) a plurality of bearing assemblies each interposed between each of said beads and said core member for allowing rotation of said core member within said beads, so that said probe is rotatable.

5. The flexible cable of claim 4,
   (a) wherein each of said beads has a rounded first end portion; and
   (b) wherein each of said beads has a rounded second end portion defining a cup-shaped cavity therein for matingly slidably receiving the first end portion of an adjacent bead.

6. The flexible cable of claim 5, wherein each of said bearing assemblies comprises:
   (a) an annular first ring member connected to the wall of each of said bead, said first ring member having an outer surface connected to the wall of said bead and an inner surface defining a bore therethrough, the inner surface having a groove extending therearound;
   (b) an annular second ring member disposed in the bore of said first ring member, said second ring member having an outer surface;
   (c) a plurality of bearings interposed between said first ring member and said second ring member, each of said bearings slidably received in the groove; and
   (d) an annular retainer interposed between said second ring member and said core member for retaining said bearing in the groove, said retainer having an outer surface slidably connected to said second ring member and an inner surface surrounding said core member.

7. The flexible cable of claim 6, further comprising a flexible sheath surrounding said core member and interposed between adjacent retainers for protecting said core member from damage.

8. The flexible cable of claim 7, wherein said core member is layered steel for resisting sheer stress while remaining flexible.

9. In a nuclear steam generator heat transfer tube having an inside surface, a flexible cable for carrying an eddy current inspection probe along the inside surface to inspect the tube, comprising:
   (a) an elongated generally cylindrical core member having the inspection probe connected to an end portion thereof for supporting the probe and having an elongated electrical conductor helically wrapped therearound and connected to the probe for conducting electrical current to the probe, said core member having an exterior surface;
   (b) a plurality of adjacent interconnecting beads disposed along the exterior of said electrical conductor for providing rigidity and flexibility to said cable, each of said beads having an inner wall defining a longitudinal bore through said bead for surrounding said electrical conductor, each of said beads having a rounded outwardly flared first end portion and having a rounded bulbous second end portion defining a generally cup-shaped cavity therein in communication with the bore for matingly slidably receiving the first end portion of an adjacent bead so that said beads are interconnected and for defining a fixed pivot point in the cavity so that each of said beads is pivotable about the pivot point;

(c) a plurality of bearing assemblies interposed between each of said beads and said electrical conductor for allowing said core member and the electrical conductor wrapped therearound to rotate within said beads so that said inspection probe is radially rotatable, each of said bearing assemblies including:

(i) an annular first ring member connected to the wall of each of said beads, said first ring member having an outer surface affixed to the wall of said bead and an inner surface defining a longitudinal bore through said first ring member, the inner surface having a groove extending therearound;

(ii) an annular second ring member disposed in the bore of said first ring member, said second ring member having an outer surface;

(iii) a plurality of spherical bearings interposed between said first ring member and said second ring member, each of said bearings slidably received in the groove; and (iv) an annular retainer interposed between said second ring member and said core member for retaining said bearings between said first ring member and said second ring member, said retainer having an outer surface connected to said second ring member and an inner surface surrounding and engaging said core member, whereby said retainer, said second ring member, and said core member are freely transversely rotatable within the bore of each of said beads so that the inspection probe is transversely rotatable and whereby the first end portion of each of said beads is slidably pivotably disposed within the cavity defined by the second end portion of an adjacent bead for allowing said cable to flex without seizing in the tube, the bore providing clearance for said bead to pivot without damaging said core member and said electrical conductor.

10. The flexible cable of claim 9, further comprising a generally cylindrical flexible sheath surrounding said electrical conductor that surrounds said core member, said sheath interposed between adjacent retainers for protecting said electrical conductor and said core member from damage.

11. The flexible cable of claim 10, wherein said sheath is a flexible plastic for allowing said cable to be flexible.

12. The flexible cable of claim 11, wherein each of said beads is a plastic material having a low coefficient of friction for allowing each of said beads to slide along the inside surface of the tube with minimal friction.

13. The flexible cable of claim 12, wherein said core member is layered steel for providing flexibility to said cable.

* * * * *

UNITED STATES PATENT AND TRADEMARK OFFICE
CERTIFICATE OF CORRECTION

PATENT NO.  : 5,174,164
DATED       : December 29, 1992
INVENTOR(S) : John J. Wilhelm It is certified that error appears in the above-identified patent and that said Letters Patent is hereby corrected as shown below:

On the title page, item [75],

The inventor's name "John J. Wilhelm" was incorrectly printed as "John J. Wilheim".

Signed and Sealed this

Second Day of November, 1993

Attest:

BRUCE LEHMAN

*Attesting Officer*  *Commissioner of Patents and Trademarks*